United States Patent [19]

Ferns

[11] 4,038,419
[45] July 26, 1977

[54] ENZYMATIC CLARIFICATION OF LIQUIDS

[75] Inventor: Ricardo Segura Ferns, Madrid, Spain

[73] Assignee: Instituto de Farmacologia Espanola, S.L. (Fundacion Marques de Urquijo), Madrid, Spain

[21] Appl. No.: 574,907

[22] Filed: May 6, 1975

[30] Foreign Application Priority Data

May 6, 1974 United Kingdom ............... 19884/74

[51] Int. Cl.$^2$ .............................................. C12H 1/12
[52] U.S. Cl. ...................................... 426/12; 195/62; 195/66 R; 426/63
[58] Field of Search .................. 195/66 R, 62; 426/12, 426/63

[56] References Cited

U.S. PATENT DOCUMENTS

| | | | |
|---|---|---|---|
| 2,988,487 | 6/1961 | Nickerson et al. | 195/62 X |
| 3,597,220 | 8/1971 | Weinrich et al. | 426/12 |

OTHER PUBLICATIONS

Kashkin et al., Preparation of proteolytic enzymes of *Streptomyces fradiae* 0072. Chemical Abstracts, vol. 81, 1974, (p. 417, 167821c).

Petrova, et al., Effect of the medium on the formation and properties of proteinases in a submerged culture of Actinomyces fradiae 119. Chemical Abstracts vol. 80, 1974 (p. 307, 144387f).

Nakata, et al., Substrate Activation and Substrate Inhibition of Trypsin-like Enzymes from Three Strains of Streptomyces Species, J. Bio. Chem., vol. 71, 1972, (pp. 1085-1088).

*Primary Examiner*—David M. Naff
*Attorney, Agent, or Firm*—Young & Thompson

[57] ABSTRACT

An enzyme protease derived from induced fermentation of *Streptomyces fradiae* is used to clarify the actual or potential turbidity of an aqueous liquid such as a beverage by adding the enzyme to the liquid in an amount such that the enzyme activity is 200,000 to 20,000,000 UA per Hl. of the liquid. Some advantages of using this protease enzyme are that it is autodestroying and is not present in a beverage after storage, that it has low toxicity and that it can be sterilized by dry heat without significant loss in activity.

3 Claims, 4 Drawing Figures

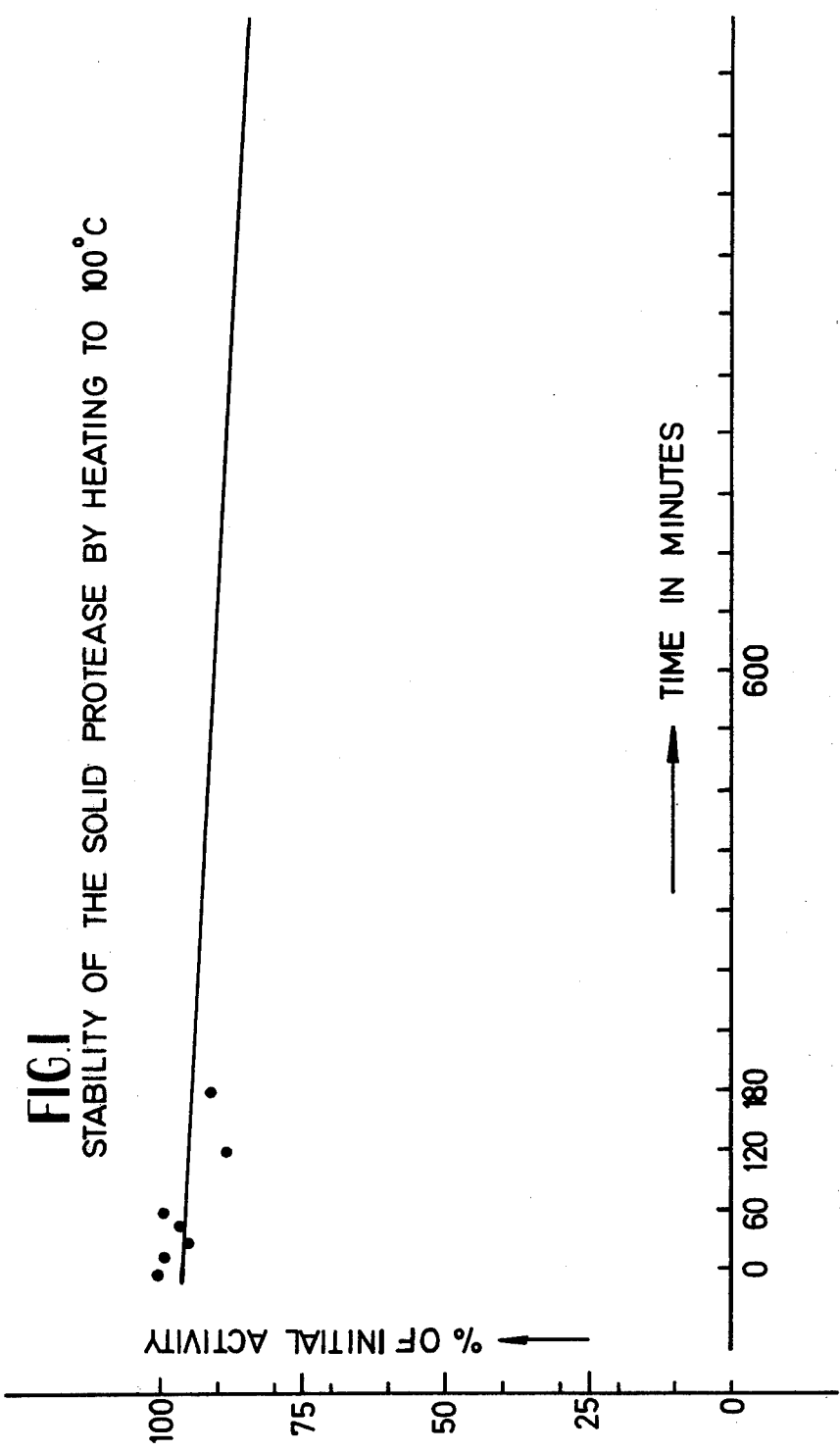

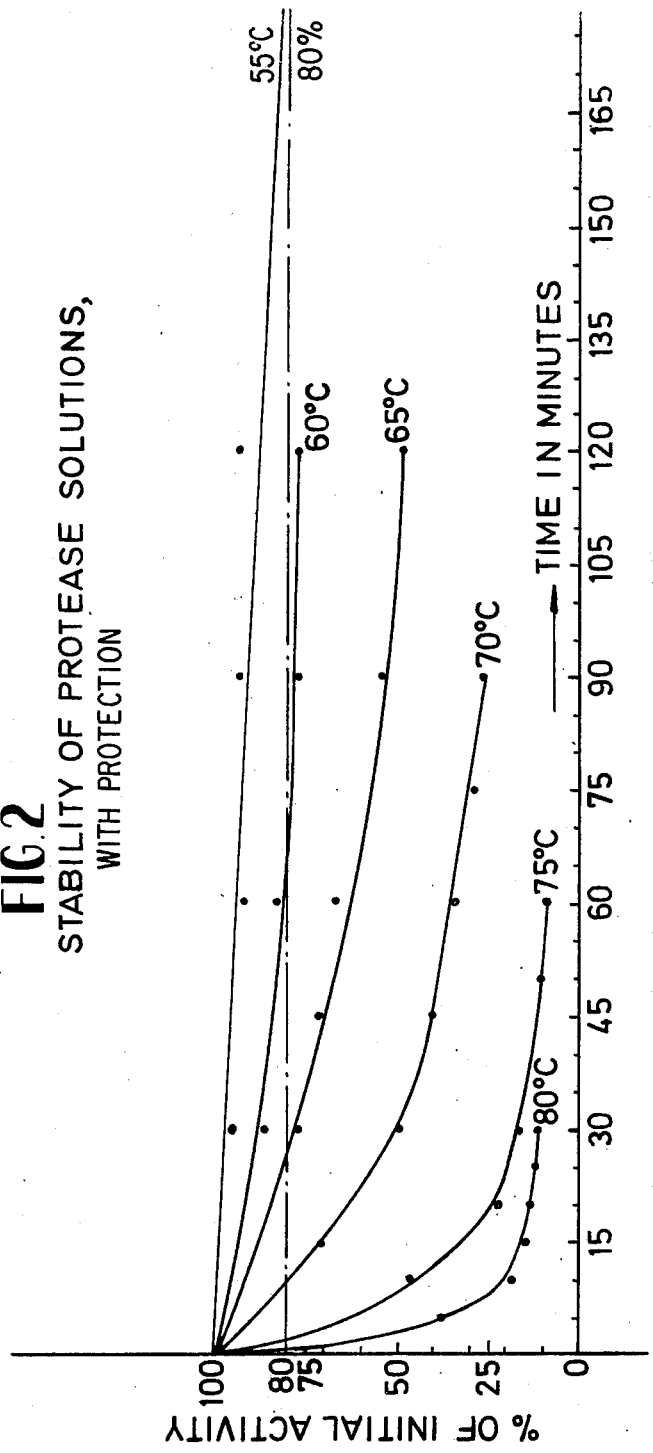

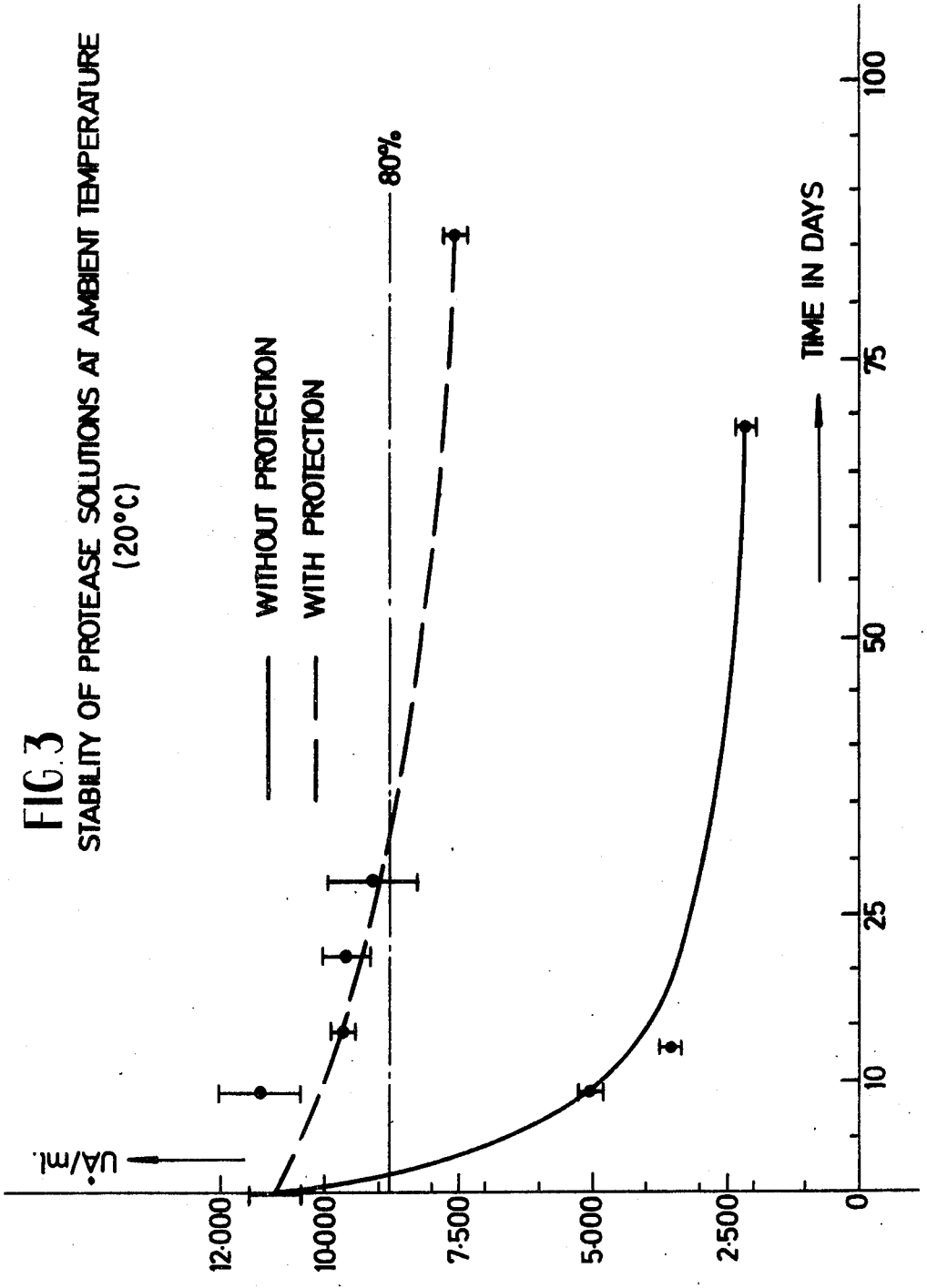

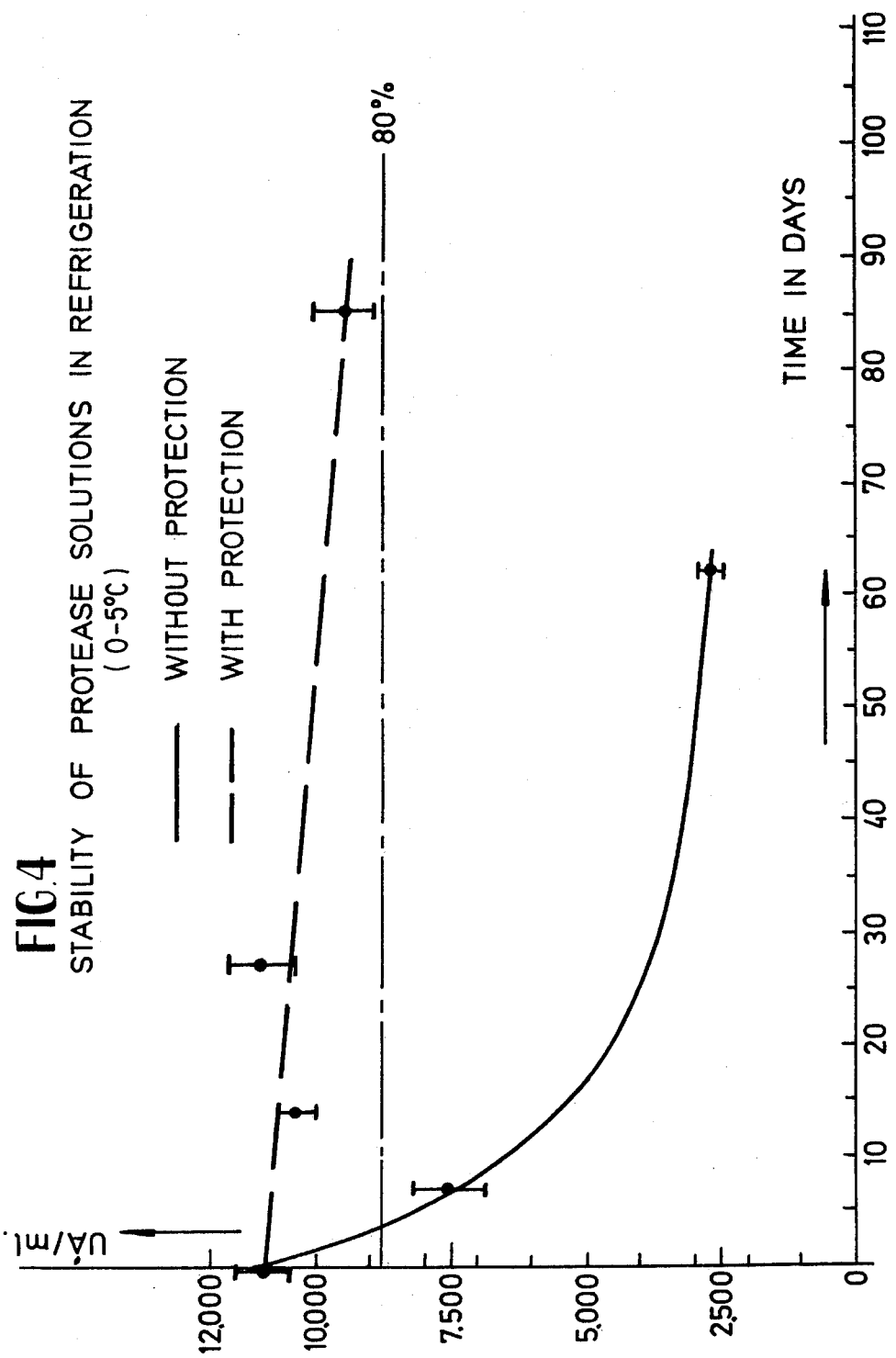

ENZYMATIC CLARIFICATION OF LIQUIDS

The invention relates to the use of a specific enzyme process for the clarification of turbid liquids or liquids capable of becoming cloudy during storage.

The importance attaching to the clarity or transparency of solutions in general is well known, more particularly in the case of drinks. Also well known are the drawbacks encountered in the clarification of such solutions by way of purely physical procedures (filtration, centrifuging, etc.), particularly when coagulable proteins are present in the solutions, above all if they are of widely differing molecular weights, in which case filtration is extremely difficult and centrifuging is frequently inefficient. Both procedures are very useful in the case of drinks with a high content of dry extract, which increases the density and viscosity in the drinks, this density and viscosity being two of the factors which affect the flow yield realized in filtration and in the classification realized in the course of filtration.

It also frequently occurs that liquids clarified by purely physical procedures again become turbid during their storage, which is easily explainable by: the increase in size of dispersed micelles, which are of large size and whose molecular structure (for example, proteins) have many points at which linkages can be formed; by genuine sinterizing; by residual Van der Waals force linkages; and, above all, by hydrogen bridges. This would explain the great magnitude of turbidity in polyphenols and tannins (as J. de Clerck clearly showed in "Bulletin de l'Association Royale des Anciens Etudiants en Braserie de l'Universite de Louvain", 68th Year, 1972, No. 1, pages 15-23). The truth is that purely physical clarification does not remove the large soluble molecules, but is limited to separating those molecules whose size exceeds the size which is critical for the procedure or technique used.

However, the biodegrading of nitrogenated substances by enzyme clarification produces a double effect, viz: 1. When the solid protein substratum is hydrolyzed, it eliminates or reduces the actually presently turbidity which, on its own, facilitates the subsequent filtration or centrifuging actions; 2. When acting on dissolved macromolecules, degrading them to small peptides, it prevents their subesequent coagulation, thus exercizing a clarifying effect on potential turbidity, which causes the clarified liquid to stay transparent while it is being stored.

These advantages, which can thus be explained theoretically, are confirmed in practice. For example, in the practical example of the beer brewing industry enzyme products, deriving from the vegetable kingdom, have been used for a long time, almost from the beginning of the century, for the clarification of beer. These enzyme products used at the present time are: those obtained from "Carica Papaya", generally in solutions rich in papain; commercial concentrates of fig latex ("Ficus glabrata"), which contains ficin as active product. Also, hydrolyzing enzymes deriving from mushrooms and from barley have been proposed.

In spite of the fact that - insofar as the clarification of turbid liquids is concerned - the results obtained with enzymes derived from papain are, frankly, good, the drawbacks, entailed in the use of such enzymes of vegetable origin, are very great. Firstly, they are relatively unstable, owing to the fact that they have to be used in enriched solutions; they are not susceptible of sterilization by thermal treatment, as they are present in solution; and they are only active within narrow pH limits. However, in addition, they are usually expensive and, as their supply depends on the harvests, the extent to which they are usuable industrially is conditioned by climatic conditions, by the geographical position of the plantations (which, in the case of papain, for example, must be located in tropical or subtropical climes), etc.

The invention seeks to eliminate such drawbacks, and, in accordance with the invention the enzyme products used are those obtained through induced industrial scale fermentation of microorganisms, more specifically of "Streptomyces", from whose medium - which is both used as a fermentation medium and as a medium enriched through fermentation techniques - is separated, in solid condition, an enzyme fraction, which is highly active for the clarification of, and for the prevention of turbidity in, aqueous protien liquids.

Thus the invention suitably consists in hydrolyzing the peptide macromolecules which are formed in these liquids and are the principal causes of actual or potential turbidity, with the assistance of an enzyme product deriving from induced "Streptomyces" culture.

Such enzymes derived from the "Streptomyces", in addition to being products obtained on an industrial scale at relatively low cost, and which - in contradistinction to the position regarding the derivatives of vegetable harvests, which become more expensive with increased demand - become cheaper with increased production, so that their use becomes more widespread, have all the advantages, which are not found with the vegetable enzymes. In addition to the fact that they are not toxic, these proteases, deriving from the "Streptomyces" and obtainable in solid condition, can be sterilized by dry heat without significant loss in activity. They can also be manipulated in sterile condition owing to their high stability in the dry state. Also, although their use in the dry condition has the advantage that it is not necessary to dilute the liquid to be clarified, the solubility of these proteases makes it possible to obtain solutions which can be stabilized if it is desired to use the enzyme by the addition to liquid to the liquid which is intended to clarify.

The liquids to be clarified must preferably be aqueous, although they do not have to be solely aqueous. It is also clear that the turbidity of these liquids, which has to be clarified, is related to the presence of peptides or proteins therein. It is also necessary to ensure that there is not, in the liquid to be clarified, antifermenting substances of the type which are specific to the enzymes used and in quantities such that these enzymes can be denatured; that there is not excessive saline concentration such as would cause "salting out" of the enzyme mixture added to the turbid liquid; and, finally, that there is not a concentration of hydrogen ions which is so high (pH $<$ 3) nor so low (pH $>$ 11) that it would prevent activiation of the enzymes in solution, or even denature these enzymes in solution. Furthermore, when the turbid liquids to be clarified contain, in addition to water, organic solvents (acetone, alcohols, glycols, etc.), the concentration of these organic solvents must not exceed a value which would render the added enzyme insoluble, and thus render it inactive, or precipitate it.

Obtaining the product, and description thereof.

A.-Obtaining the product.

The proteolytic enzymes used as clarifiers are preferably obtained by inoculation of Streptomyces fradiae on an agar plate, by sowing the inocula in fermentation flasks charged with sterile nutrient medium, by stirring and sterile aeration, and by sowing the inocula developed in the intermediate flasks in sterile fermentation tanks which are charged with a nutrient medium which contains mineral salts, sugar and sufficient nitrogenated contribution to carry out fermanentation at a specific pH value and with controlled temperature and sterile aeration. When fermentation has been completed, the (culture) medium is filtered and precipitated in acetone, and the solid dry product contains the enzyme activity of the (culture) media.

B.-Proteolytic activity.

The proteolytic activity becomes clearly apparent by activating the enzymes opposite protein substrata, which may be in the form of casein, azocasein, keratin, haemoglobin, etc. Haemoglobin has been found to be a useful substratum for the quantitative stimulation of the enzyme activity, Anson's method being used (J.Gen.-Physiol. 22: 79, 1938); and, in the invention the enzyme products used are evaluated as clarifiers in Anson units.

The proteolytic enzyme is in the form of a whitish powder with a strength of 4000 to 10000 UA/mg, the particular value depending on the particular manufacturing batch. When the enzyme has been subjected to electrophoresis, four fundamental bands have been shown to separate, when this electrophoresis is carried out on noble agar gel (Difco) in veronal/sodium veronal buffers, at a pH of 8.2 and with an ion strength of 0.035, for a period of some 80 minutes, and a spacing of 10 cm between salt bridges, with deposition of the sample 2 cm from the bridge connected to the anode, consuming 3.5 mA/cm gel at a mean voltage of 10.9 volts/cm, and giving relative mobilities in accordance with the following table:

| FRACTION | RELATIVE MOBILITY |
|---|---|
| A | 0.5 |
| B | 0.7 |
| C | 0.8 |
| D | 1.0 |

Generally speaking, the protein of fraction A is that containing the largest percentage (35%), the remaining protein content being divided among the other fractions in approximately equal percentage amounts.

In carrying out an electrophoretic analysis of the enzyme under experimental conditions similar to those described, it is clear that all the protein fractions are enzyme fractions, haemoglobin also being used as active substratum, and the digestion spots being revealed by coloration of the protein base with Ponceau red; and that fraction A is that with the greatest enzyme activity, followed by fraction C, and then by fractions B and D, whose activity values are approximately equal to one another.

There may be, within the homogeneity of fractions, quantitative differences between fermentation batches, without alteration - for the different enzyme proportions - in the clarification results realized in the turbid liquids; this is because they behace as isoenzymes, with great similarity between the fractions. Also, appreciable differences in specificity can be observed.

The optimal pH value for activating the enzyme solution, and the pH value optimal for the stability of the enzyme solution, is close to the neutral pH value, viz 6 to 8, which coincides with the optimal value desired for industrial liquids used in drinks, both for human and animal nourishment.

C.-Stability.

In their dry state, the solid enzymes are remarkably stable to the action of temperature, and this can be exploited in their sterilization.

The accompanying drawings are graphs showing various aspects of the stability of protease and protease solutions according to the present invention, in which:

FIG. 1 is a graph of the stability of the solid protease heated to 100° C., in terms of percentage of initial activity versus time in minutes;

FIG. 2 is a graph of the stability of protease solutions, with protection, at various temperatures, with the same ordinates and abscissae as in FIG. 1;

FIG. 3 is a graph of the stability of 20% protease solutions at ambient temperature, with and without protection, in terms of UA/ml versus time in days; and FIG. 4 is a graph similar to FIG. 3 but with refrigeration.

The following Table, which is summarized in FIG. 1, indicates the stability at 100° C of a solid protease as a function of the heating time.

| TIME IN MINUTES | ACTIVITY IN UA/mg. | % RETENTION OF THE INITIAL ACTIVITY |
|---|---|---|
| 0 | 8.532 | 100 |
| 15 | 8.406 | 99 |
| 30 | 8.029 | 95 |
| 45 | 8.139 | 96 |
| 60 | 8.411 | 99 |
| 120 | 7.436 | 88 |
| 180 | 7.684 | 91 |
| 1320 | 6.955 | 82 |

The usual fluctuation in the curve can be explained by the limits of exactness of the Anson method for the quantitative evaluation of proleolytic enzymes, and also the appearance of an increase in the activity may derive from a loss in the dessication of moisture and volatile substances, with consequent enrichment of the active solid substance.

The stability of the solutions of the protease is a function of the temperature at which they are stored, and also of the presence of stabilizing ions in the activation medium.

The calcium ion has been shown to have a notable stabilizing action, even in relatively small concentrations. FIG. 2 plots the retained activity, along the ordinate, against the heating time, set out in minutes along the abscissa, the different temperatures at which this heating is carried out being set out in the action lines of the graph.

The analogous plot of stability/time, at ambient temperature and in the absence of calcium ion, is set out in FIG. 3, in which the activity is represented in UA/ml along the ordinate and the actuation period is set out in days along the abscissa.

FIG. 4 shows the stability of the protease solution stored under refrigereated conditions (temperature 0° to 5° C) for a period of some three months, and makes it clear that, over a period of time of this order, its deactivation amounts, in the presence of calcium ion, to less than 20% of the initial activity.

As a summary of the work carried out, and comparing the stability data set out in the last three graphs referred to, it is possible to state that:

1. The product is susceptible of being handled as a solution and of being stored in dissolved conditions in industries such as the beer brewing industry, which have available ordinary refrigerating units (at 5° C, and over a period of three months, the loss of activity is greater than 20% of the initial activity).

2. For clarification operations, and for rapid protein degradation (break up), the dissolved product can be used at different temperatures higher than ambient temperature, without, for an appreciable time, the activity of the stabilized solution decreasing above 20%. At a temperature of 55° C the maximum period will be 3 hours; for a temperature of 60° C, a perid of a 1 hour; and at a temperature of 65° C, for approximately half an hour, while at a temperature of 70° C the period will be about ten minutes. Above 70° C, the average life of the enzyme is of the order of minutes.

3. It is interesting to note that the enzyme is auto-destroying at ambient temperature for a period greater than 100 days in the case of solutions with calcium protection (defence), while the enzyme will have an average life of some 9 days without calcium protection; when this enzyme is used in the drinks industry, a sufficient addition can be controlled for clarifying the drink and for maintaining it in clarified condition during its storage. However, as the enzyme will be auto-destroying after its clarifying function has been fulfilled, the drinker will not be dosed or overdosed with active enzyme products; if this auto-destruction were not to take place, it could involve pharmacological, legal, and even health complications. The ultrastable enzymes in solution retain their detectable pharmacological and enzyme action after their clarifying function has been carried out, so that secondary effects in the ingestion of the clarified, processed substances can be felt by the consumer of the drink.

D.-Toxicity.

The toxicity of the product has been studied toxicologically from the two points of view of acute toxicity, orally administered, and chronic toxicity, also orally administered.

Acute toxicity tests have been carried out on mice, using enzyme products of very differnt fermentation batches, of course of the test being followed from the point of view of mortality, case rate (morbidity; sickness), and growth curve. The dose added to the test diet was of the order of 1,000,000 UA/kg. of fodder administered. In all instances a perfect health condition was observed (tests lasting from 10 to 30 days) in the group of mice tested, to whose food proteases had been added, with an improvement in the growth curve relative to the simultaneous control group. There were no mortalities in any of the recorded tests.

The tests for chronic toxicity were carried out on recently born chicks, who were fed with feeding stuff to which the enzyme derived from *Streptomyces fradiae* was added, the tests being abandoned when the chicks were 9 to 10 weeks old. In all cases the health condition of the chicks to whom enzymes had been fed was equal to, or better than, that of the control chicks, who had been fed with the same fodder to which enzymes had not been added.

The absence of toxicity from the proteolitic enzymes of Streptomyces enables the enzymes to be used in medicine, and at the present time they are being used in pharmaceutical preparations, combined with antibiotics for facilitating their absorption.

DESCRIPTION OF THE METHOD.

It is neither feasible nor practicable, owing to the large number of possible variations in the generic problem of the clarification of turbid liquids, the revelant factors to be taken into account including the cause of the turbidity, the degree of this turbidity, the possibility of modifying the pH value of the liquid to be treated, the stability to heating of the liquid, the period of storage of the liquid after it has been clarified, the intrinsic composition itself of the clear liquid, etc., to give detailed and uniform handling instructions of a general nature. Such instructions for clarifying the turbid liquids must match the specific conditions presented by the liquid to be clarified in each instance occurring in practice. However, all these variations in detail will be variations from the common essential norms to which the process, embodying the invention, are subjected, and which they may be specified in the following general way:

The addition, to the liquid to be clarified, of the enzyme product from "Streptomyces" fermentation, may take place once or a number of times. The addition of the enzyme product of times will be particularly useful when large nitrogenated molecules have to be treated at relatively high temperatures. The enzyme product can be added in solid condition, dissolved in water or in aqueous solution, with or without the presence of calcium ion, or dissolved in part of the liquid to be clarified itself.

The liquid on which the enzymes must act should preferably not be of an acidity such as to give a pH value lower than 3 nor be of an alkalinity such as to give a pH value greater than 10. The same pH limits should be maintained for solution liquids when the dissolved enzyme product is added.

The concentration of the enzyme product to be added will depend, within very wide limits, on the specificity of the enzyme in respect of the nitrogenated substream which has to be hydrolyzed, but generally the enzyme activity will vary between 200,000 and 20,000,000 UA per Hl. of liquid to be clarified.

The turbid liquid, to which the enzyme component has been added, can be stored, or filtered with subsequent storage, bearing in mind that if, at low temperatures (0 to 5° C), the clarifying action is slower, the mean life of the enzyme, by which clarification is carried out, is prolonged. At ambient temperatures (18° to 25° C) the action (activity) is more rapid, and the decline is greater so that, in practice, the same clarifying result is arrived at as in cold solutions, although it takes place in less time. When the temperature is increased to about 55° to 60° C, the clarifying process is shortened appreciably, as is also the average life of the enzyme. It is possibly (by checking the average life of the enzyme in separate tests, the activity being followed by the quantitative analytical method of Anson) to predict the instant at which it will be necessary, if it is desired to continue the enzyme action at moderately high temperature, to make successive additions of enzymes for maintaining a sufficient level of active concentration of enzyme.

If, at any instant, it is desired to stop the enzyme action, or to destroy the residual active enzyme (when this is considered to be necessary), it suffices to prolong the time of storage of the clear liquid in accordance with the stability graphs already referred to and which accompany the specification, to heat the clear solution for a few minutes to a temperature above about 90° C, to raise the pH value of the clear solution above 10, or to lower the pH value to below 3 (the original pH value can be restored quickly).

The process embodying the invention is further illustrated in, the following specific Examples.

EXAMPLE 1

DETERMINATION OF THE CLARIFYING EFFECT OF STREPTOMYCES FRADIAE PROTEASE ON RESIDUAL TURBIDITY IN AQUEOUS SOLUTIONS OF FILTERED COMMERCIAL GELATIN

TECHNIQUE EMPLOYED

The turbidity is determined by dispersion of monochromatic light caused by the solid particles in dispersion (Tyndall effect) in the protein solution.

The dispersed light is read at an angle of 90° to the incident light, and the recorded value of the dispersed light is checked at the same wavelength as that of the incident light. The intensity of the dispersed light is directly proportional to the quantity of the particles causing the turbidity of the liquid subjected to test.

METHOD

Two silver, commercial quality gelatin solutions are prepared in the same concentration, and by means of the same procedure, as is described below, an enzyme solution, prepared in the stated manner, was added to part of these gelatin solutions.

In all instances the intensity of the incident light was adjusted to a suitable value for allowing recording to be carried out subject to the stated experimental conditions, when monochromatic light was incident upon the most turbid solution of the series (the control solution). Without modification in the intensity of the incident light, intensity of the dispersed light was recorded for each solution of gelatin, to which solution deactivated protease (see mode of procedure) has been added, and solution of active protease was added to the other portion of the other solution, and was incubated in the stated conditions. This was carried out for the purpose of obtaining a reference target in each turbid solution brought to the same concentration and subject to the same conditions as the test solution to be investigated, naturally with the exception of the enzyme activity present in the test solutions and absent from the control solutions.

The intensity of the dispersed light was an indication of the concentration of solids in dispersed condition, that is to say of the turbidity.

The wavelength selected for the test coincides with the wavelength at which the intensity of the dispersed light is the greatest.

EXPERIMENTAL METHOD

Preparation of a gelatin solution in borate buffer.
pH = 8.2 Conc. = 0.05M 75 g of commercial quality silver gelatin are weighed and are added to about 700–800 cc of borate buffer (pH = 8.2, Conc. = 0.05M), which has previously been heated to 70° to 80° C. The solution is shaken, the said temperature being maintained until the gelatin is completely dissolved. The hot solution is filtered (at 50° to 60° C) on paper and in vacuo, so as to remove the larger-sized particles and, when filtration has been completed, the volume of the solution is made up to 1 liter with borate buffer.

Preparation of a solution of active protease in borate buffer

Three grams of a Streptomyces protease, with an activity of 11,626 UA/mg (about 35 million UA in toto), are dissolved, with mechanical shaking in about 150 ml borate buffer (pH = 8.2; Conc. = 0.05M). The solution is filtered over Supercel cake and, when filtration has been completed, the volume is made up to 200 ml with the same buffer, and 250 mg of anhydrous calcium chloride and 50 ml of propylene glycol are added as stabilizer.

The solution prepared in this way has an activity of about 100,000 UA/ml.

Preparation of deactivated protease solution 125 ml of the previous solution of active protease is boiled for 10 minutes so as to deactivate the enzyme. After this 10 minutes, the solution is allowed to cool to ambient temperature, and is made up, with borate buffer, to the initial volume (125 cc).

The solution thus treated is without enzyme activity.

Preparation of a solution of gelatin with deactivated protease.

(Control solution).

50 ml of deactivated protease solution are added to 200 ml of gelatin solution.

Preparation of a gelatin solution with active protease.

(Test solution).

50 ml of active protease solution (100,000 UA/ml) are added to 200 ml of gelatin solution, the test solution remaining with an activity of 20,000 UA/ml.

INCUBATION

As soon as the test and the control solutions have been prepared, they are placed in a drying oven at 35° C, and are kept there for 24 hours.

When this 24 hours has ended these solutions are withdrawn from the oven, and the supernatant liquid is taken from both solutions so as to measure their respective turbidities. It can be seen by inspecting the supernatant liquids with the naked eye that the control solution is cloudy, whereas the test solution is clear and transparent.

DETERMINATION OF THE TURBIDITY BY DIFFRACTION

Use was made of a ZEISS RPQ-20 spectrophotometer, together with spectrum fluorometry accessories, made by the same firm. The light source used was a xenon lamp with stabilized supply, readings being carried out at a constant amperage of 2.5 A, with cooling pre-filter and selection of incident monochromatic light by a double effect monochromator (ZEISS MM 12). The equipment worked with an aperture of 1.4 mm, and wavelength of 462 m$\mu$.

The working tank was made of quartz, its dimensions being 1 × 1 cm, with a transparent base (readings at 90°), and the recording spectrophotometer was adjusted for intensity measurements, the dispersed light being recorded at the same wavelength, viz. 462 m$\mu$, and with an aperture of 1.4 mm.

In all instances, all the above-stated conditions were maintained unaltered, and also the amplification of the diffracted light, and the 0 to 100 and maximum intensity adjustment. It was found, that under experimental conditions, the clean distilled water has an intensity less than 2% (corresponding to turbidity = 0), and the most cloudy solution adjusts the intensity reading, as stated, to a value close to 100.

EXPERIMENTAL RESULTS

Determinations were made on 4 groups of solutions, control and test, obtained on different days.

Eight turbidity readings were obtained from each control and test solution, and the mean value result of each group, and also the limits of reliability for a value of 95% of probability in the normal dispersion statistical curve, are set out in the following Table:

|  | CONTROL SOLUTION | | | | TEST SOLUTION | | | |
|---|---|---|---|---|---|---|---|---|
|  | A | B | C | D | A | B | C | D |
| No of cases | 8 | 8 | 8 | 8 | 8 | 8 | 8 | 8 |
| Vm-t DS | 104 | 101 | 96 | 101 | 30 | 41 | 25 | 20 |
| Vm | 102 | 96 | 93 | 96 | 28 | 39 | 24 | 19 |
| Vm-t DS | 100 | 91 | 90 | 91 | 26 | 37 | 23 | 18 |
| Variability Index | 3% | 6% | 3% | 5% | 6% | 7% | 5% | 4% |

As can be seen, there are no great and important differences between average values of 4 series of each example (control and test), of each statistical group, which indicates a good reproductivity of the method. Accordingly, the 4 series of 8 readings can be summarized in a single mean value for each series which is given in the following Table:

|  | CONTROL SOLUTION | TEST SOLUTION |
|---|---|---|
| No of cases | 32 | 32 |
| Vm-t DS | 99 | 31 |
| Vm | 97 | 28 |
| Vm-t DS | 95 | 25 |
| Variability Index | 2% | 26% |

ANALYSIS OF RESULTS

As will be understood from the preceding Table, the intensity of the dispersed light due to the turbidity is reduced, under the described experimental conditions for treatment and for determination, by the enzyme clarification process (forming the subject matter of this invention) from about 97 ± 2 (i.e. close to the value 100) to 28 ± 3. Thus, a clarification of almost 70% is achieved.

EXAMPLE 2

CLARIFICATION BY FILTRATION OF A GELATIN SOLUTION BY MEANS OF STREPTOMYCES PROTEASES AS FILTRATION ACCELERATOR

TECHNIQUE EMPLOYED

Relatively concentrated solutions of gelatin can be clarified by filtration employing special filter papers, with large pores. Although they eliminate the larger suspended particles, they do not achieve perfect clarification owing to the pore size. At all events, the operation is slow and tedious.

One cause of the slowness is the relatively high viscosity of these solutions at ambient temperature.

With the use of Streptomyces protease solutions, added to the gelatin solutions, a marked reduction is achieved in the viscosity of the medium, and this — in the handling (manipulation) of a filtration, results in an appreciable shortening of the filtration time for achieving (even with ordinary or slow filtration papers) a more rapid and more perfect separation, by filtration of solid and liquid owing to the use of filter papers whose pores are smaller.

METHOD

The method used consisted in determining viscosities and filtration times, in standard equipment, of solutions of gelatin, to one part of which an active solution of Streptomyces protease was added (the test solution), and to the other part of which the same quantity of thermally deactivated Streptomyces protease was added (control solution).

EXPERIMENTAL METHOD

Test solution: Solution of gelatin with Streptomyces protease identical to that in Example 1.

Control solution: Solution of gelatin with deactivated Streptomyces protease, identical to that of Example 1.

INCUBATION

The oven at 37° C, for 24 hours, as in Example 1.

When the prescribed incubation period was over, both solutions (i.e. control and test solutions) were removed from the oven, and were homogenized by shaking, before proceeding to the determinations of viscosity and filtration speed.

Determination of viscosity: The determinations were carried out with a CANNON-FENSKE viscosimeter, with double levelling, fed in all instances with the same volume of liquid. Constant K of the viscosimeter = 0.014009 for 15.56° C = 60° F; 0.0139900 for 37.78° C = 100° F; 0.013975 for 54.44° C = 130° F; (all the values of K are in cSK/sec).

To the clean viscosimeter, which had been placed in a thermostatic bath at 20° C, was added the volume of test liquid, the assembly being kept in the bath until thermal equilibrium is attained.

There was carried out, in each determination of emptying time between marks, the time being recorded with a timekeeping watch having a scale capable of reading to a one-fifth of a second, a respective determination with distilled water under identical conditions.

Each time determination was made for two consecutive readings which, in the working conditions, were identical to one another.

RESULTS

The emptying times, proportional to the kinematic viscosity and, hence, in direct relationship with the filtration time of each test, are summarised in the following Table,

|  | EMPTYING TIME (SECONDS) | | |
|---|---|---|---|
|  | CONTROL | TEST | DISTILLED WATER |
| No. of cases | 6 | 6 | 6 |
| Vm-tDS | 469 | 106 | 75.6 |
| Vm | 358 | 105 | 74.8 |
| Vm-tDS | 247 | 104 | 74.0 |
| Variability Index | 29.6% | 0.8% | 1% | and in the following Table which also includes the deduced values of kinematic viscosity obtained by multiplying the emptying time of each solution by the constant of the viscosimeter at 20° C (data interpolated).

| KINETIC VISCOSITY at 20° C (in cSK) | | | |
|---|---|---|---|
| | K = 0.014006 | | |
| | CONTROL | TEST | DISTILLED WATER |
| No. of cases | 6 | 6 | 6 |
| Vm-tDS | 6.568814 | 1.484636 | 1.0588536 |
| Vm | 5.014148 | 1.470630 | 1.0476488 |
| Vm-tDS | 3.459482 | 1.456624 | 1.0364440 |
| Variability Index | 29.57% | 0.85% | 1% |

ANALYSIS OF RESULTS

There is a large variation in kinematic viscosity in the gelatin solutions of the controls (mean value = 5.014; variability index = 30%).

The gelatin solutions of the test examples (to which active Streptomyces protease was added) homogenize remarkably in respect of kinematic viscosity, which reduces the mean value = 1.471 (variation index = 0.85%), which represents a reduction in viscosity of 70.7%, the viscosity of the substance treated by the method embodying the invention remaining very close to the viscosity of the distilled water (Vm = 1.048; variation index = 1%). (Treated substances Vm = 1.471 as opposed to medium value, water = 1.048. Control examples, without treatment, Vm = 5.014 as opposed to Vm, water = 1.048).

FILTRATION

Simultaneously, and with the same solutions in which the viscosity determinations are made, a determination was made of the filtration time in standard conditions through filter paper derived from the first manufacturing batch, the time taken for collecting 10 cc being timed, after the first 5 cc had been passed, in accordance with Tappi's method, with charges of 20 ml of filtering liquid.

EQUIPMENT

Three conical funnels of 55 mm diameter and height of 45 mm, with stem of 53 mm and internal diameter of the stem of 4 mm, terminated with pen (feather) cut, were placed on a 25 ml test-tube, and above each was placed Schleicher-Schull No. 589³ paper filter, of 10 cm diameter, without folding with the exception of a single fold required for giving the paper disc the exact shape of the funnel which, bent over on itself, remained facing the inside of the cone and stuck to the wall of the cone.

At ambient temperature, working singly, a recording was made of the time required for collecting from 5 cm of the filtrate to 15 cm thereof. At least 6 checks were made of the filtration time of each solution, and the following Table gives the results of the mean value of each group, and also the limits of reliability for a certainty of 95% of probability in the statistical curve of normal dispersion:

| | CONTROL | | | TEST | | | DISTILLED WATER | | |
|---|---|---|---|---|---|---|---|---|---|
| | A | B | C | A | B | C | A | B | C |
| No. of cases | 6 | 8 | 9 | 6 | 6 | 7 | 6 | 6 | 9 |
| Vm-tDS | 1.506 | 1.445 | 1.527 | 510 | 480 | 560 | 149 | 135 | 127 |
| Vm | 1.271 | 1.234 | 1.288 | 432 | 403 | 437 | 127 | 119 | 117 |
| Vm-tDS | 1.037 | 1.023 | 1.049 | 354 | 325 | 314 | 105 | 103 | 107 |
| 100 DS/ | | | | | | | | | |

-continued

| | CONTROL | | | TEST | | | DISTILLED WATER | | |
|---|---|---|---|---|---|---|---|---|---|
| | A | B | C | A | B | C | A | B | C |
| Vm | 17% | 20% | 24% | 17% | 18% | 30% | 17% | 13% | 11% |

As can be seen, there are no significant differences statistically between mean values of three series of each example (test, controls and distilled water check) of each group, which indicates a good reproductivity of the method and homogeneity in the pores of the paper, so that each of the three series of six minimum readings can be summarized in a single mean value in each series, given in the following Table:

| | CONTROL | TEST | DISTILLED WATER |
|---|---|---|---|
| No of cases | 23 | 19 | 21 |
| Vm-tDS | 1377 | 471 | 128 |
| Vm | 1265 | 425 | 121 |
| Vm-tDS | 1153 | 379 | 113 |
| 100 DS/Vm | 20.51% | 22.53% | 13.30% |

ANALYSIS OF CONCLUSIONS

The enzyme treatment appreciably reduces the filtration time of 1265 seconds of the solution which has not been given enzyme treatment (the control solution) to 425 seconds in the case of the solution treated by the procedure embodying the invention (i.e. the test solution). Thus, it reduces the time by 66.4% approximately and, comparing the filtration times in proportion to the filtration time of water under the same conditions, it will be seen that: filtration time of the control solution = 10.45 times the filtration time, under the same conditions of distilled water; the filtration time of the test solution = 3.51 times the filtration time, under the same conditions, of distilled water.

This makes it fully clear that the treatment has been effective and has brought the filtration time of a slow protein filtration liquid close to the filtration time of pure distilled water under identical experimental conditions.

EXAMPLE 3

CLARIFICATION OF A VISCOUS LIQUID WITH TURBIDIFYING PROTEIN THROUGH THE ACTION OF STREPTOMYCES FRADIAE PROTEASES

TECHNIQUE EMPLOYED

A viscous solution of gelatin with borate buffer was prepared, and was subdivided into equal portions.

There was added, to each aliquot portion, an exactly weighed and fixed quantity of a solid protein turbidifying substance, which was insoluble in the viscous solution.

A constant volume of Streptomvces protease solution, having a variable activity per ml, was added to each cloudy (turbid) mixture. The different suspensions being clarified were incubated, and were finally passed to a centrifuge tube whose base is a cylinder which had a lesser diameter than that of the mouth portion, which is also cylindrical, of 1 ml capacity, the small outer cylinder being graduated in units of 0.02 ml and, logically, its end portion closed hemispherically.

All the test solutions, contained in the said tubes (which are identical to one another), are simultaneously centrifuged.

When centrifuging has been completed, the turbidifying substance has been found to have settled in the small graduated terminal cylinder, on whose graduation the apparent volume of the solid residual turbidifying substance can be read, this reading indicating the turbidity in each instance.

EXPERIMENTAL METHOD

Preparation of gelatin solution in borate buffer (pH = 8.2; Conc. = 0.05M)

75 g of commercial quality silver gelatin were dissolved in 1 liter of borate buffer (pH = 8.2; Conc. = 0.05 M) in the same manner as in Example 1.

Preparation of a solution of active Streptomyces Fradiae protease in borate buffer 0.6 g of a Streptomyces fradiae protease, with an activity of 11,626 UA/mg (about 7 million UA in toto) were dissolved, with mechanical shaking, in about 150 cc of borate buffer (pH = 8.2; Conc. = 0.05M). The solution was filtered on Supercel cake and, when filtration had been completed, the volume was made up to 200 cc in the same buffer, and 250 mg of anhydrous calcium chloride and 50 ml of propylene glycol were added as stabilizers. The solution thus prepared had an activity of about 20,000 UA/ml.

Preparation of a solution of deactivated Streptomyces Fradiae protease (control solution)

125 ml of the previous active protease solution was boiled for 10 minutes so as to deactivate the enzyme. When this 10 minutes had passed, the solution was allowed to cool to ambient temperature, and was made up, with borate buffer, to the initial volume of 125 ml. The solution was without enzyme activity.

Preparation of a gelatin solution with casein turbidifier and increasing quantities of active protease solution Exactly 2 g of casein were weighed and placed in 600 cc flasks, and to each of these flasks 40 cc of gelatin solution were gradually added, shaking taking place so that there was initially formed a paste which facilitated the formation of a homogeneous suspension.

There was added, to this series of suspensions: 0, 2, 4, 6, 8 and 10 ml of active Streptomyces protease, and 10, 8, 6, 4, 2 and 0 ml respectively of deactivated Streptomyces protease, with the result that the final volume was 50 ml in all units of the series, and so that they contained approximately: 0, 40,000, 80,000, 120,000, 160,000 and 200,000 UA/flask. Thorough homogenization was carried out, and they were introduced into an oven for incubation.

INCUBATION

In the oven at 37° C for 24 hours, as in Example 1. After this 24 hours, they are withdrawn from the oven, and centifuging is carried out.

CENTIFUGING

Six centrifuge tubes were used, whose base was a cylinder graduated from 0.02 to 100 ml, of lesser diameter than the mouth, which was also cylindrical, the measurements of the upper cylinder being: inner diameter = 14 mm; height = 52 mm. The measurements of the lower cylinder were: inner diameter = 2.6 mm; height = 50 mm.

5 ml of each suspension was passed to a centrifuge tube, after thorought homogenization, and the whole series was simultaneously centrifuged at 3,000 r.p.m., for 8 minutes.

After centrifuging, the volume of sediment was read, on the graduated scale, for each protease concentration, the operation being repeated 6 times so as to obtain a statistical series.

The mean value, limits of reliability, and index of variability were set out in the following Table.

| UA/FLASK | UA/ml. | Vm-tDS | Vm | Vm-tDS | 100 DS/Vm |
|---|---|---|---|---|---|
| 0 | 0 | 0.61 | 0.57 | 0.53 | 6.5% |
| 40,000 | 800 | 0.23 | 0.19 | 0.15 | 19.7% |
| 80,000 | 1,600 | 0.10 | 0.09 | 0.08 | 11.0% |
| 120,000 | 2,400 | 0.09 | 0.08 | 0.07 | 20.0% |
| 160,000 | 3,200 | 0.06 | 0.06 | 0.06 | 0.0% |
| 200,000 | 4,000 | 0.04 | 0.03 | 0.02 | 31.0% |

ANALYSIS OF RESULTS

In tests in which the quantity of turbidifier (casein) was lower than 2 g per aliquot portion, clarification carried out by the enzyme is total, without any perceptible sediment being noticed in the base of the centrifuge tube.

An inverse relationship is to be noted between residual turbidity and the concentration of Streptomyces protease, that is to say there is a continuous reduction in detectable sediment with increase in the activity.

By modifying the concentration in UA/ml of the Streptomyces fradiae protease added, it is possible to proceed from a total clarification to a partial clarification according to particular requirements.

(For all the preceding Examples, 1, 2, and 3, the value "t" refers to Student's $t$ for a probability of 95%, and in accordance with n (the number of data present in the arithmetic mean).

EXAMPLE 4

Fifteen g of Streptomyces fradiae protease, in dry condition and with a unitary strength of 11,000 UA/mg, were dissolved, with shaking and at ambient temperature, for 1 hour, 4 g of dry calcium chloride having previously been added to the buffers.

When shaking has been completed, the enzyme solution was filtered, subjected to suction and through an ordinary filter paper covered "in situ" by a washed, dry diatomic cake of about 5 mm height.

When filtration had been completed, the cake, which had been drained in vacuo, is washed twice with 100 ml of buffers, the cake being drained after each washing and the discharging liquids being collected on the filtration mother liquors. The collected, transparent filtrate liquors was homogenized, and 100 ml of propylene glycol were added to these filtrate liquors, the pH value being adjusted to a value of 6.0 by an addition of sodium hydroxide solution.

The proteolitic activity of the enzyme solution was evaluated by Anson's method (J. Gen Physiol. 22: 79, 1938) and, from the analytical data obtained, it was possible to deduce the quantity of buffers which it was necessary to add to the filtered enzyme solution to adjust its enzyme strength to 250,000 UA/ml.

For the clarification of beer this solution was used, 3 ml being added per Hl. of beer to be clarified, following the American method, after the initial filtration, consequent upon the primary fermentation. The beer was stored for 6 weeks in the starting tank, to which the enzyme solution was added.

When the action (activity) phase had been completed, the second filtration takes place, and then the clean beer was pasteurized and conditioned, the beer then passing to a bottling station and then being passed for final storage.

The transparency results of the beer stored at ambient temperature, and with thermal shock, are set out in Table No. 1, there also being included in this table the results of tests carried out in parallel with two commercial enzyme preparations obtained by concentration of plant sap (juice).

It will be appreciated that the clarification results achieved in the comparative test carried out are clearly favourable to the use of proteases derived from Streptomices fradiae, both for the absolute initial brilliance and also for the maintenance of the clear solution, comparing the results with those obtained in the first manufacturing batch, clarification being carried out with commercial products commercially in use by the beer brewing industry.

Table No. 2 summarizes the relative increase in turbidity of the beers clarified with the commerical products in use at the present time, as compared with that of beer clarified by the method embodying the invention.

It will be clearly seen that the residual filtration turbidity of beers is, for those beers treated with proteases derived from Streptomices, about 18 ± 5% lower than that of the same beers treated with proteases of vegatable origin; and that the turbidity developed during storage, at ambient temperature, increases more rapidly in the beers treated with vegetable proteases up to 71% greater turbidity. Equally good comparative results are obtaned with thermal shock.

The great advantages of the method which has been described, and embodies the invention, may be summarized as follows:

1. Utilization of a product, without specific toxicity when administered orally at the doses used, which makes this product applicable for the clarification of nourishing drinks.

2. The possibility of facilitating clarification, by filtering or centrifuging, of cloudy liquids, including liquids whose turbidity is not of protein nature, when the nitrogenated macromolecules are the cause of the high viscosity or density of the cloudy liquid, and degrade, by hydrolysis caused by the enzyme, to smaller molecules, with simultaneous reduction in the density or viscosity.

3. A protective effect for preventing the occurrence of turbidity during storage of the clarified liquid.

4. The specific action of the Streptomyces enzymes in respect of the protein substratum make the method particularly suitable for cloudy solutions in which the turbidifier is of peptide nature, and in which there are no peptide structures which have to be maintained whole in the clarified liquid, as the enzyme can act simultaneously both on the peptide structures and on the turbidifier. However, apart from this exception, the enzyme leaves unaltered all the other structures (apart from carbamides) of the essential composition of the liquid, for example: sugars, dyes, artificial sweeteners, synthetic thickeners, aromatic esters, etc. Expressed in other words, it may be stated that, in contradistinction to purely chemical treatments, there is no substantial alteration to the composition of the clarified liquid insofar as the great majority of its constituents is concerned.

5. Including the case of liquids to be clarified which are essentially of protein nature, and are turbid accidentally or by chance, the possible degradation of the essential protein by the clarification carried out by means of this process is not a major drawback, because this degradation leads to the formation of assimilable products which, as they are more easily absorbable, will have equal or greater nourishing qualities; and, for this reason, this method can be the most recommedable one in the case of nourishing drinks, including those of protein nature.

6. As a consequence of the specificity of its action, the method usually leads to the formation of clear products without alteration in flavour, taste or odour of the liquid before and after the treatment. This point has been statistically confirmed, with specialized taste-removing agents in the case of beers clarified by the method embodying the invention.

7. The comparative lability (instability) of the solutions of Streptomyces enzymes makes it possible, through the use of simple techniques (which include simply storage), to provide for the total elimination of the residual enzyme activity.

TABLE No. 1

| TEST CONDITIONS | TEST DURATION IN DAYS | TURBIDITY INDEX | | | |
|---|---|---|---|---|---|
| | | Prot. of Strept. | Prot. Vegetable 1 | Prot. Vegetable 2 | Prot. Vegetables Vm |
| | 0 (Initial Brilliance) | 0.36 | 0.44 | 0.41 | 0.425 |
| SHELF | 15 | 0.36 | 0.46 | 0.49 | 0.475 |
| LIFE | 30 | 0.33 | 0.45 | 0.47 | 0.46 |
| AT | 60 | 0.28 | 0.49 | 0.47 | 0.48 |
| AMBIENT | 15 | 0.37 | 0.50 | 0.53 | 0.515 |
| TEMPER- | | 2.7 | 8.6 % | 8.0 % | 0.3 % |
| ATURE | 30 | 0.37 | 0.52 | 0.56 | 0.54 |
| | | 12 % | 15 % | 19 % | 17 % |
| | 60 | 0.31 | 0.52 | 0.54 | 0.53 |
| | | 10 % | 6 % | 14 % | 10 % |
| THERMAL | Ambient | 0.37 | 0.52 | 0.54 | 0.53 |
| SHOCK FROM | 0° C | 0.72 | 1.13 | 1.33 | 1.23 |
| 60° C to 0° C | | 94 % | 117 % | 146 % | 131.5 % |

TABLE No. 2

% of turbidity of bears clarified with streptomyces protease (standard · 100%) as compared with vegetable proteases in industrial use for different storage periods, at ambient temperature and with thermal shock, 0 - 60° C.

| TEST CONDITIONS | TEST DURATION IN DAYS | Streptomices Protease TURBIDITY = | Protease Vegetables 1 TURBIDITY = | Protease Vegetables 2 TURBIDITY = | Protease Vegetables Vm TURBIDITY = |
|---|---|---|---|---|---|
| AMBIENT TEMP. | Initially = 0 | 100 % | 122.2 % | 113.9 % | 118.1 % |
| | 15 | 100 % | 131.5% ± 3.7% | 139.7% ± 3.6% | 135.6% ± 3.7% |
| | 30 | 100 % | 138.5% ± 2.1% | 146.9% ± 4.5% | 142.7% ± 3.3% |
| | 60 | 100 % | 171.4% ± 3.6% | 171.0% ± 3.2% | 171.2% ± 0.2% |
| THERMAL SHOCK | Ambient | 100 % | 140.5 % | 145.9 % | 143.2 % |
| | 0° C | 100 % | 156.9 % | 184.7 % | 170.8 % |
| | | 100 % | 124.5 % | 155.3 % | 139.9 % |

What is claimed is:

1. A method for the clarification of turbidity, and for the prevention of turbidity in, aqueous liquid beverages comprising the steps of producing a proteolytic enzyme by fermentation of Streptomyces fradiae in a culture medium, separating said proteolytic enzyme from said medium, forming a solution of said proteolytic enzyme in a said aqueous liquid beverage, and maintaining said solution for a predetermined time at a predetermined temperature sufficient to clarify the actual or potential turbidity of the liquid beverage by said proleolytic enzyme hydrolyzing protein materials in said beverage that cause said turbidity; the temperature of the solution being from 0° to 85° C., the pH of the solution being from 3 to 10, and the activity of said proteolytic enzyme in the solution being 200,000 to 20,000,000 UA per hectoliter.

2. A method as claimed in claim 1, in which the temperature of the solution is ambient temperature.

3. A method as claimed in claim 1, in which the enzyme is added in successive batches to the liquid.

* * * * *